United States Patent [19]
Swerdloff et al.

[11] Patent Number: 5,661,773
[45] Date of Patent: Aug. 26, 1997

[54] INTERFACE FOR RADIATION THERAPY MACHINE

[75] Inventors: Stuart Swerdloff, San Francisco, Calif.; Thomas Rockwell Mackie; Timothy Holmes, both of Madison, Wis.

[73] Assignee: Wisconsin Alumni Research Foundation, Madison, Wis.

[21] Appl. No.: 477,055

[22] Filed: Jun. 7, 1995

Related U.S. Application Data

[60] Continuation-in-part of Ser. No. 191,243, Feb. 2, 1994, Pat. No. 5,528,650, which is a division of Ser. No. 854,521, Mar. 19, 1992, Pat. No. 5,317,616.

[51] Int. Cl.$^6$ ....................................................... A61N 5/01
[52] U.S. Cl. .................................................. 378/65; 378/69
[58] Field of Search .................................. 378/64, 65, 68, 378/69

[56] References Cited

U.S. PATENT DOCUMENTS

| | | | |
|---|---|---|---|
| 4,230,129 | 10/1980 | LeVeen | 128/804 |
| 4,233,519 | 11/1980 | Coad | 250/514 |
| 4,247,774 | 1/1981 | Brooks | 250/367 |
| 4,367,411 | 1/1983 | Hanley | 250/492.2 |
| 4,397,314 | 8/1983 | Vaguine | 128/399 |
| 4,660,799 | 4/1987 | Butland | 248/676 |
| 4,726,046 | 2/1988 | Nunan | 378/65 |
| 4,794,629 | 12/1988 | Pastyr et al. | 378/152 |
| 4,817,125 | 3/1989 | Skelbitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/152 |
| 4,987,309 | 1/1991 | Klasen et al. | 250/492.1 |
| 5,297,037 | 3/1994 | Ifuku | 364/413.15 |
| 5,418,827 | 5/1995 | Deasy et al. | 378/65 |

FOREIGN PATENT DOCUMENTS

| | | |
|---|---|---|
| 0 034 735 | 9/1981 | European Pat. Off. . |
| 0 037 008 | 10/1981 | European Pat. Off. . |
| 0 048 402 | 3/1982 | European Pat. Off. . |
| 0 083 198 | 7/1983 | European Pat. Off. . |
| 0 113 879 | 7/1984 | European Pat. Off. . |
| 0 144 670 | 6/1985 | European Pat. Off. . |
| 0 161 324 | 11/1985 | European Pat. Off. . |
| 0 209 930 | 1/1987 | European Pat. Off. . |
| 0 251 407 | 1/1988 | European Pat. Off. . |
| 0 253 060 | 1/1988 | European Pat. Off. . |
| 0 259 989 | 3/1988 | European Pat. Off. . |
| 0 286 858 | 10/1988 | European Pat. Off. . |
| 0 314 214 | 5/1989 | European Pat. Off. . |
| 0 371 303 | 6/1990 | European Pat. Off. . |
| 0 387 801 | 9/1990 | European Pat. Off. . |
| 0 387 921 | 9/1990 | European Pat. Off. . |
| 0 417 965 | 3/1991 | European Pat. Off. . |
| 0 449 113 | 10/1991 | European Pat. Off. . |
| 0 460 749 | 12/1991 | European Pat. Off. . |
| 0 464 645 | 1/1992 | European Pat. Off. . |
| 0 498 438 | 8/1992 | European Pat. Off. . |
| 0 514 971 | 11/1992 | European Pat. Off. . |
| 2.023.648 | 8/1970 | France . |
| 2 346 754 | 10/1977 | France . |

(List continued on next page.)

OTHER PUBLICATIONS

Optimization by simulated Annealing Of Three–Dimensional Conformal Treatment Planning For Radiation Fields Defined by a Multileaf Collimator, S. Webb, *Phys. Med. Biol.* 1991 vol. No. 9, 1201–1226 no month.

(List continued on next page.)

*Primary Examiner*—David P. Porta
*Assistant Examiner*—David Vernon Bruce
*Attorney, Agent, or Firm*—Quarles & Brady

[57] ABSTRACT

A human interface to be used with irradiation machine in a computed tomography machine wherein x-ray computed tomography images are individually display on a computer screen and an operator uses a manual cursor control device to trace various irradiation zones on the image, identify desired dose within each zone, verify the accuracy of the therapy treatment plan prior to an irradiation session, and verify irradiation delivered after a therapy treatment session.

14 Claims, 11 Drawing Sheets

FOREIGN PATENT DOCUMENTS

| | | |
|---|---|---|
| 30 48 682 | 9/1981 | Germany . |
| 36 21 868 | 1/1988 | Germany . |
| 86/01919 | 3/1986 | WIPO . |
| 89/11826 | 12/1989 | WIPO . |
| 90/09812 | 9/1990 | WIPO . |
| 93/03793 | 3/1993 | WIPO . |

OTHER PUBLICATIONS

On The Use Of Cimmino's Simultaneous Projections Method For Computing A Solution Of The Inverse Problem In Radiation Therapy Treatment Planning, Y. Censor, M. D. Altschuler & W. D. Powlis, *Inverse Problems 4* (1988) 607–623 no month.

A Constrained Least–Squares Optimization Method For External Beam Radiation Therapy Treatment Planning, G. Starkschall *Med. Phys.* 11 (5), Sep./Oct. 1984.

Optimization of Conformal Radiotherapy Dose Distributions by Simulated Annealing, S. Webb, *Phys. Med. Biol.* 1989, vol. 43, No. 10, 1349–1370 no month.

Calculation and Application of Point Spread Functions For Treatment Planning With High Energy Photon Beams, Ahnesio et al., *Acta Oncol.* 26:49–56; 1987 no month.

Methods of Image Reconstruction From Projections Applied to Conformation Radiotherapy, Bortfeld, et al., *Phys. Med. Biol.* 35(10), 1423–1434; 1990 no month.

Feasibility solutions in Radiation Therapy Treatment Planning, Altschuler et al., *IEEE Comp. Soc.* 1984:220–224 no month.

Optimization of Stationary and Moving Beam Radiation Therapy Techniques, Brahme, *Radiotherapy and Oncol.* 12:129–140; 1988 no month.

A Unified Approach to the Optimization of Brachytherapy and External Beam Dosimetry, Holmes et al., *Int. J. Rad. Oncol. Biol. Phys.*, vol. 20, 859–873, 1991 no month.

Wedge–Shaped Dose Distributions By Computer–Controlled Collimator Motion, Kijewski, et al., *Med. Physics,* vol. 5, No. 5 (1978) no month.

5,661,773

INTERFACE FOR RADIATION THERAPY MACHINE

This is a continuation in part of U.S. patent application Ser. No. 08/191,243 entitled METHOD AND APPARATUS FOR RADIATION THERAPY which was filed on Feb. 2, 1994, now U.S. Pat. No. 5,528,650, issued on Jun. 18, 1996, which in turn is a division of application Ser. No. 07/854,521 now U.S. Pat. No. 5,317,616 entitled METHOD AND APPARATUS FOR RADIATION THERAPY which issued on May 31, 1994.

FIELD OF THE INVENTION

This invention relates generally to radiation therapy equipment for the treatment of tumors, or the like, and specifically to a human interface for designating and verifying radiation dose placement within a patient, and for generating radiation dose maps for use in radiation therapy.

BACKGROUND ART

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}$Co, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radioopaque mask of arbitrary outline.

As part of collimating the beam to the outline of the tumor, the offset angle of the radiation beam, with respect to a radius line between the radiation source and the center of rotation of the radiation source, may be adjusted to allow the treated area to be other than at the center of rotation. Simultaneously changing the offset angle and the width of the radiation beam as a function of gantry angle allows tumorous tissue having an irregular cross-section within a plane parallel to the radiation beam to be accurately targeted. The width and offset angle of the radiation beam may be controlled by the use of a multiple-leaf collimator.

Adjustment of the offset angle, center, and size of the radiation beam at various gantry angles allows considerable latitude in controlling the dose. Nevertheless, these approaches still impart a considerable amount of undesired dose to healthy tissue, especially where the tumor is concave or highly irregular.

U.S. Pat. No. 5,317,616, which issued on May 31, 1994, describes a compensator that dynamically controls the effective intensity of rays within a radiation beam to produce a fluence profile of arbitrary shape. This ability to vary the intensity of individual rays within the beam, as opposed to simply turning them on or off, allows an advanced technique of therapy planning to be employed in which fluence profiles can be varied at each gantry angle to accurately control the dose to irregularly shaped tumors within the body. An efficient iterative approach allows precise calculation of the needed fluence profiles. Preferably, this compensator is used with a radiation source to direct radiation toward one slice at a time.

While this compensator can provide highly resolved control of the intensity of radiation received throughout a volume of a patient, as the degree of control increases, the burden on a machine operator to specify and verify dose can become increasingly burdensome. For example, specifying intensity of individual rays of a radiation fan beam at each of hundreds of different beam orientations with respect to a tumorous volume is a time Consuming and labor intensive process. The inconvenience of this complex planning protocol is exacerbated where the protocol must be followed separately for each of a plurality of patient slices. Where ray intensities have been identified for each gantry orientation and each patient slice and a test simulation indicates that the combined irradiation dose of all rays is erroneous, correction of the radiation plan would be extremely burdensome. Moreover, where a dose error has been made during a treatment session either due to poor planning or unexpected dose absorption or penetration, correction would also be difficult.

SUMMARY OF THE INVENTION

The present invention is a human interface to be used with a radiation therapy machine as described above which allows a user to identify various radiation zones within a slice of a patient, the interface pictorially representing the patient slice as a tomographic image including a portion of a tumor to be treated. After different irradiation zones within a tomographic image have been identified, the interface allows the operator to specify various radiation doses for each irradiation zone, to run a test simulation which takes into account radiation scatter during a therapy session to derive a theoretical pre-radiation dose map based on the doses specified by the operator, to easily change the doses specified by the operator as a function of the theoretical pre-radiation dose map that results, to verify radiation dose after a therapy session, and to plan for subsequent therapy sessions based on dose delivered during previous therapy sessions.

The interface includes a computer having a display screen, a key board, and a tracing instrument such as a mouse, electronic pencil, or the like.

It is one object of the invention to provide a radiation zone identifying means which is simple to use and is reliable.

With a sinogram displayed on the display screen, the tracing instrument can be used to circumscribe irradiation zones thus dividing the sinogram into separates zones to be treated separately from adjacent zones. Using the tracing instrument to guide a circumscribing cursor arrow on the display screen, any number different irradiation zones can be identified during a therapy planning session.

Another object of the invention is to provide simple means for assigning different radiation doses to irradiation zones. Again, the tracing means can be used to identify different zones and the key board can be used to specify different radiation doses within each irradiation zone.

Yet another object of the invention is to provide an apparatus that an operator can use to specify zones where no radiation should be delivered. No radiation zones can be identified in the same manner as described above.

A further object of the invention is to allow an operator to easily alter the quantum of radiation directed toward each zone identified on a tomographic patient slice image where a test pre-radiation therapy session indicates that treatment sinogram based on the identified zones and corresponding doses would be unacceptable. After a desired dose map has been identified using the inventive human interface, the method and apparatus described in the above identified application can be used to produce fluence profiles corresponding to a plurality of angles about the patient slice for which the dose map was generated. The fluence profiles together define a treatment sinogram corresponding to the associated dose map. Using the fluence profiles, the computer can generate a test pre-sinogram tomographic image theoretically indicating how radiation would be delivered to a patient based on the fluence profiles. Upon a perusal of the pre-radiation tomographic image an operator can determine whether or not the defined dose map and corresponding fluence profiles will provide acceptable radiation to each zone within the patient slice. Based on unacceptable radiation dispersement as evidenced by the pre-radiation tomographic image, the operator can use the interface, including the tracing instrument, to specify irradiation zones for which the identified dose should be altered and then can use the key board to alter the doses accordingly. Thereafter, the operator can run an additional test pre-radiation therapy session using the computer to determine whether or not the altered doses will provide a more acceptable dose arrangement.

Yet another object of the invention is to provide an interface that can be used to observe radiation delivered during a therapy session which can be used to alter radiation doses during later therapy sessions. By identifying the radiation entering and exiting a patient along each ray of a beam the radiation absorbed along each ray from each gantry angle can be identified and a post-treatment tomographic image associated with the patient slice can be provided. The human interface of the present invention can be used to observe the post-treatment tomographic image and compare the post-treatment image to the desired dose map to identify treatment errors. Where a treatment error (i.e. over or under radiation) has occurred, the error can be noted using the human interface and can be used to alter desired dose maps during later therapy sessions to compensate for the errors.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DETAILED DESCRIPTION OF THE PREFERRED EMBODIMENT

Figure 1:
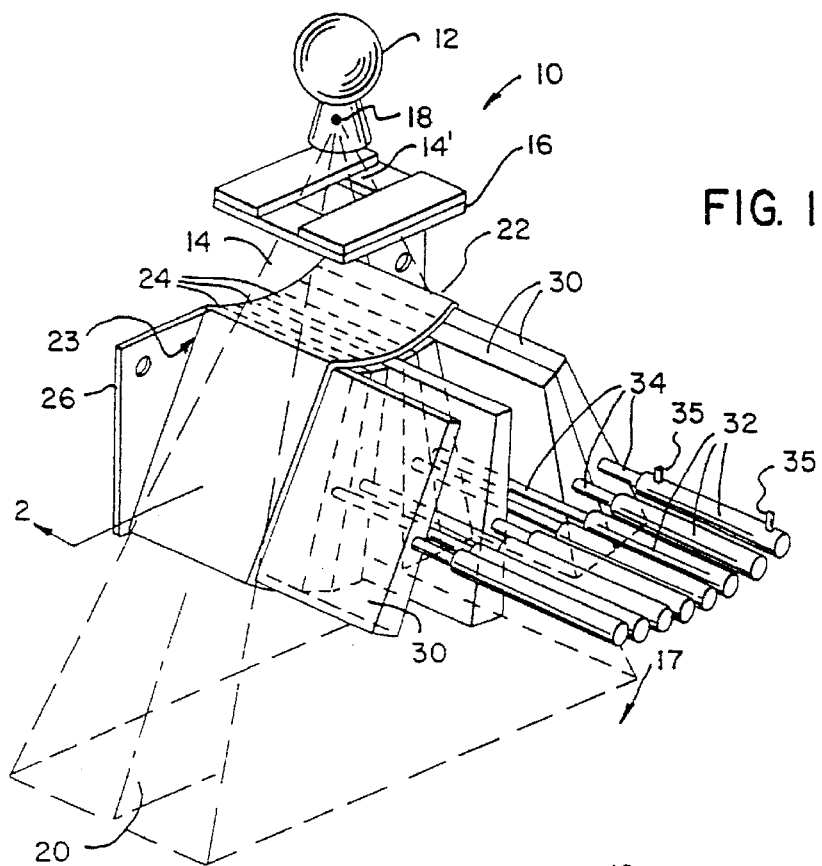
FIG. 1 is a perspective view of the compensator assembly used in the present invention, showing the compensator leaves and their associate pneumatic cylinders.

Referring to FIG. 1, a radiation therapy unit 10 suitable for use with the present invention includes a radiation source 12 producing a generally conical radiation beam 14' emanating from a focal spot 18 and directed towards a patient 17 (not shown in FIG. 1). The conical beam 14' is collimated by a radiation opaque mask 16 constructed of a set of rectangular collimator blades to form a generally planar fan beam 14 centered about a fan beam plane 20.

I. The Compensator

A compensator 22 is centered in the fan beam 14 and about the fan beam plane 20, prior to the radiation being received by the patient 17, and includes a plurality of adjacent trapezoidal leaves 30 which together form an arc of constant radius about the focal spot 18. The leaves 30 are held in sleeves 24. The sleeves 24 are constructed of radio translucent materials and attached at their inner ends 23 to a mounting plate 26 which is fixed relative to the focal spot 18. The mounting plate 26 is constructed of a sturdy, radiopaque material and is positioned Just outside the fan beam 14 to prevent interference with the fan beam 14.

Figure 2:
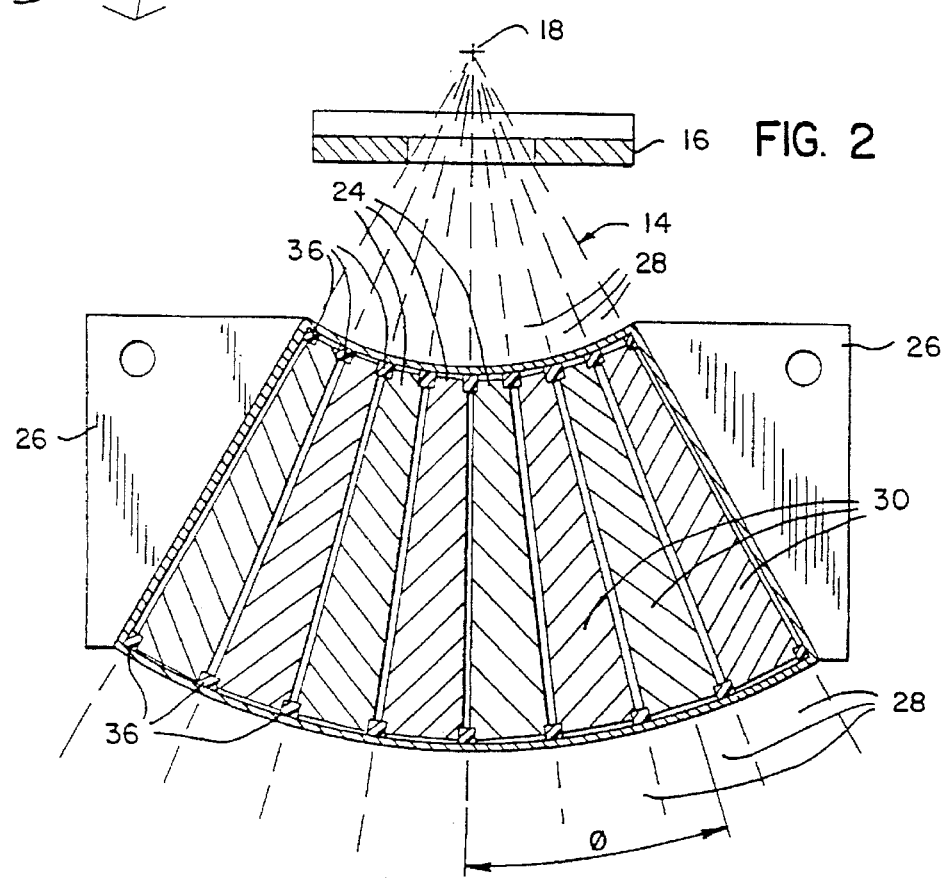
FIG. 2 is a cross-section of the compensator assembly of FIG. 1 along line 2—2 showing the trapezoidal aspect of each compensator leaf, for a fan beam of radiation, and the guide rails for supporting the compensator leaves when they move.

Preferably, the leaves 30 of the compensator 22 subtend the entire fan beam 14 to divide the fan beam 14 into a set of adjacent slab-like rays 28 at offset angles f. Referring also to FIG. 2, each sleeve 24 is open at its outer end 27 to receive, by sliding, a comparably sized trapezoidal leaf 30 constructed of a dense, radiopaque material such as lead, tungsten, cerium, tantalum or a related alloys.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the fan beam 14, so as to leave its corresponding ray 28 completely unobstructed, and yet to still be guided by the sleeve 24. In this non-blocking position, a leaf is referred to as being in the "open state".

Each leaf 30 may be moved rapidly between its open and closed states by means of a corresponding pneumatic cylinder connected to the leaf 30 by a flexible link 34. The pneumatic cylinders 32 have internal pistons (not shown) that may be moved at high velocity between the ends of the cylinders 32 by means of pressurized air coupled to the cylinders 32 through supply hoses 35. The supply hoses 35 are fed by a compensator control (not shown in FIGS. 1 or 2) to be described below. The pneumatic cylinders 32 are capable of applying high forces to the leaves 30 to move them rapidly and independently between the open and closed states.

Figure 3:
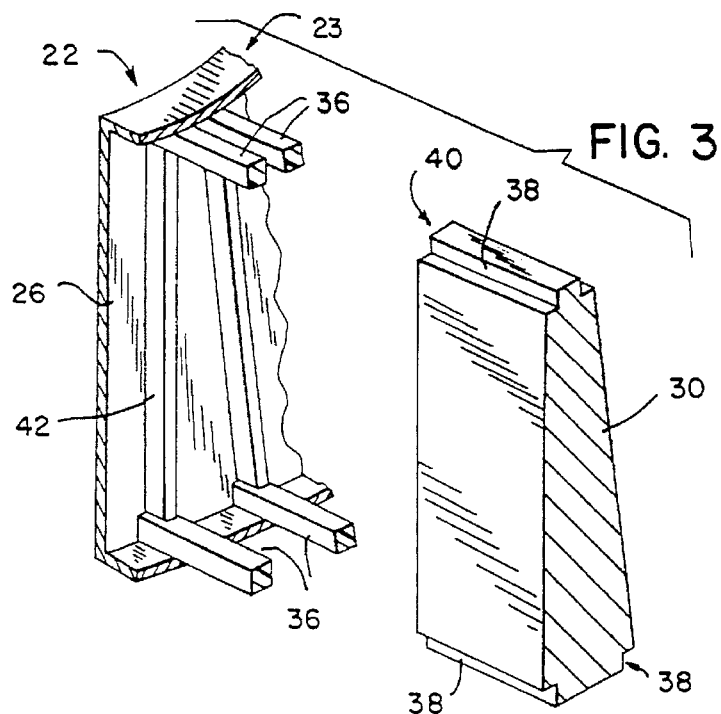
FIG. 3 is a cutaway perspective view of a set of guide rails and one leaf of FIG. 2 showing a collar for supporting the leaf in its fully closed position.

Referring now to FIGS. 2 and 3, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the fan beam 14. Whereas the guide rails 36, which are ideally radio translucent, are relatively insubstantial, in contrast, the collar 42, positioned outside the fan beam 14 on the mounting plate 26, need not be radio-translucent and hence is more substantial in construction. A collar (not shown) similar to collar 42, supports each leaf 30 when it is fully in the open state. Because the leaves 30 spend most of their time fully in the open or closed states, they are, at most times, firmly located by a supporting collar 42.

II. Radiation Therapy Hardware

Figure 4:
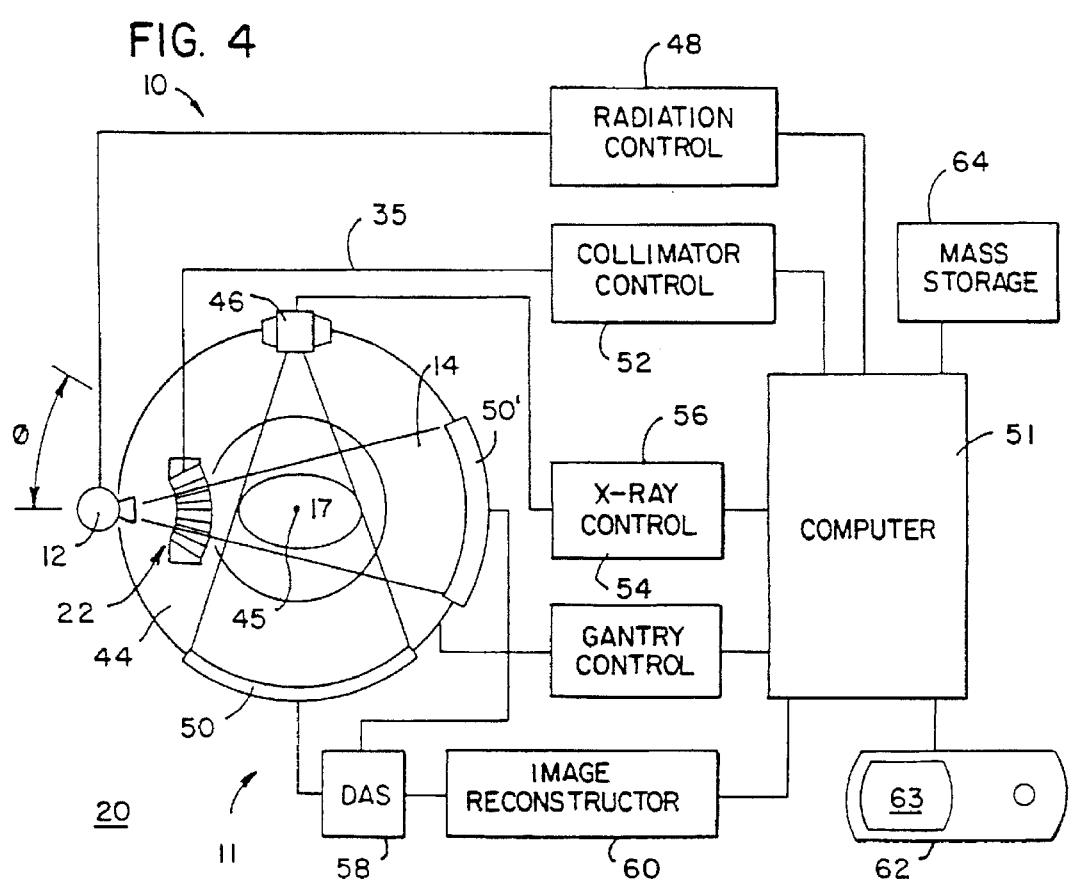
FIG. 4 is a block diagram showing the elements of a radiation therapy apparatus incorporating a conventional CT scanner and the compensator of the present invention and including a computer suitable for controlling that compensator per the present invention.

Referring now to FIG. 4, the radiation source 12 is mounted on a gantry 44, the latter rotating within the fan beam plane 20 about a center of rotation 45 in the patient 17 so that the fan beam 14 may irradiate a slice of the patient 17 from a variety of gantry angles θ.

The radiation source 12 is controlled by a radiation control module 48 which turns the radiation beam 14 on or off under the control of a computer 51.

A compensator control module 52 provides a source of compressed air and valves to gate that air through supply hoses 35 to control, separately, the pneumatic cylinders 32 to move each of the leaves 30 in and out of its corresponding sleeve 24 and ray 28 (see also FIG. 1). The compensator control module 52 also connects with computer 51 to allow program control Of the compensator 22 to be described.

A tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the angle θ of the fan beam 14 for the radiation therapy, as well as for the computed tomography x-ray source 46 and detector array 50 also attached to gantry 44. Gantry control module 54 connects with computer 51 so that the gantry may be rotated under computer control and also to provide the computer 51 with a signal indicating the gantry angle θ to assist in that control.

Control modules for the tomographic imaging system 11 include: x-ray control module 56 for turning on and off the x-ray source 46, and data acquisition system 58 for receiving data from the detector array 50 in order to construct a tomographic image. It will be understood to one of ordinary skill in the art that a detector array 50' may also be placed to receive radiation from the radiation source 12 through the patient 17 to assist in verification of the treatment.

An image reconstructor 60 typically comprising a high speed array processor or the like receives the data from the data acquisition system 58 in order to assist in "reconstructing" a tomographic image from such data according to methods well known in the art. The image reconstructor 60 also communicates with computer 51 to assist in high speed computations used in the present invention as will be described below. The tomographic image allows verification of the patient setup just prior to radiation therapy treatment.

A terminal 62 comprising a keyboard and display unit 63 allows an operator to input to programs and data to the computer 51 and to control the radiation therapy and tomographic imaging equipment 10 and 11 and to display tomographic images produced by the image reconstructor 60 on the display 63. Operation of the display and other interface hardware will be described in more detail below. A mass storage system 64, being either a magnetic disk unit or tape drive, allows the storage of data collected by the tomographic imaging system 11 for later use.

Computer programs for operating the radiation therapy system 10 will generally be stored in mass storage unit 64 and loaded into the internal memory of the computer 51 for rapid processing during use of the system 10.

During operation of the radiation therapy unit 10, the compensator control module 52 receives from the computer 51 a fluence profile for each gantry angle. The fluence profile describes the intensity or fluence of each ray 28 of the radiation beam 14 from the radiation source 12 that is desired for that gantry angle θ at a given position of the patient support table (not shown) as translated through the radiation beam 14. Together, the fluence profiles for each gantry angle make up a treatment sinogram for a particular position of the patient table (i.e. for a particular slice of the patient including a portion of the tumor).

The compensator control module 52 moves the leaves 30 of the compensator 22 rapidly between their open and closed states to either fully attenuate or provides no attenuation to each ray 28. Gradations in the fluence of each ray, as needed for each fluence profile, are obtained by adjusting the relative duration during which each leaf 30 is in the closed position compared to the relative duration during which each leaf 30 is in the open position, for each gantry angle. The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below.

The fluence profiles of the treatment sinogram are determined by therapy planning software (described below) and stored in the computer 51.

III. Therapy Planning Software

Figure 13:
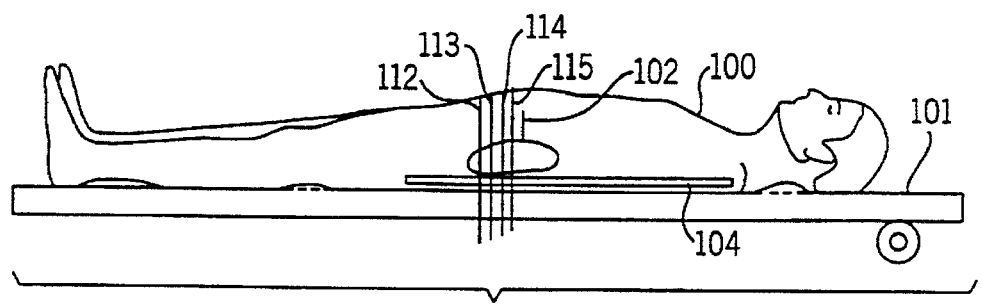
FIG. 13 is a schematic representation of a patient on a treatment table having a tumorous region.
Figure 14:
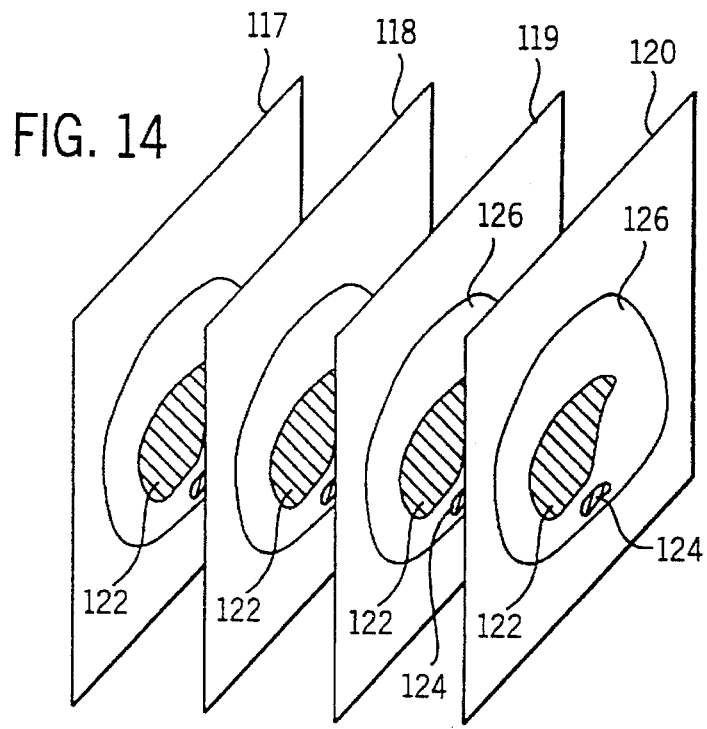
FIG. 14 is a schematic representation of four adjacent tomographic image corresponding to the patient and tumor of FIG. 13.

Referring to FIG. 13, a patient 100 resting in a supine position on a treatment table 101 has a tumorous growth 102 adjacent a spinal region 104. A treatment region 106 to be irradiated is defined as being between two slices through the patient 100 perpendicular to the upper surface of the table 101, a first defining slice 108 including an end portion of the tumor 102 and the second defining slice 110 including the other end portion of the tumor 102. The treatment region 106 is divided into a plurality of adjacent patient slices some of which are labeled 112, 113, 144, and 115. Referring also to FIG. 14, four tomographic images 117, 118, 119, 120 corresponding to the four patient slices 112, 113, 114, and 115 in FIG. 13 can be observed. Each image includes a tumorous region generally represented as 122, a spinal region generally represented as 124, and a non-tumorous tissue region represented as 126. While the tomographic images 117–120 are similar, each varies slightly and hence must be considered separately in order to provide for precise irradiation. To this end, a distinct treatment sinogram is generated for each separate tomographic image.

The generation of a treatment sinogram needed to obtain the full benefits of the above described compensator is performed by specially developed software running on the computer 51 and reconstructor 60. Although the treatment planning is performed in software, it will be recognized that the planning may also be implemented in discrete electronic circuitry dedicated to this operation and that such dedicated circuitry may be employed to provide even greater speed to this process.

Figure 5A:
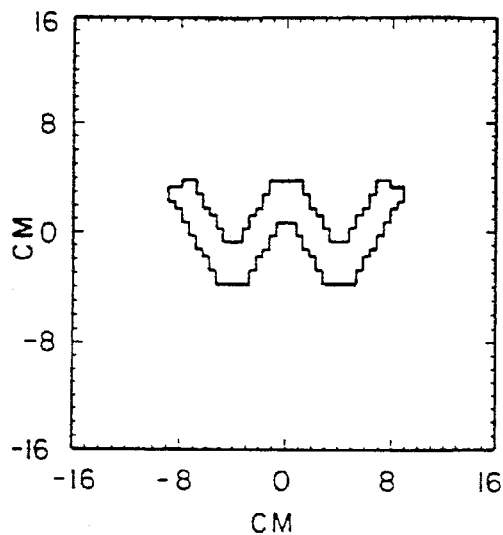
FIGS. 5(a)–(d) are dose distributions of a hypothetical tumorous region showing dose intensity by lines of equal dose, with FIG. 5(a) showing a desired dose distribution and FIGS. 5(b), (c), and (d) showing progressive actual dose distributions after two, three and ten iterations per present invention.

Referring to FIG. 5(a), the generation of the desired treatment sinogram to control compensator 22 begins with the definition of a desired dose map 66. A typical desired dose map 66 assigns a relatively high radiation dose, within a dose constraint, to an area of tumorous tissue 68 and a second lower radiation dose to the area of healthy tissue 70 outside of that region. The healthy tissue 70 may include an area 72 including a radiation sensitive organ or the like to which an even lower radiation dose may be assigned.

The desired dose map 66 is stored within the memory of computer 51 as an array of elements each element holding one digital value. The inventive method and apparatus for generating desired dose maps area described in more detail below.

Figure 6:
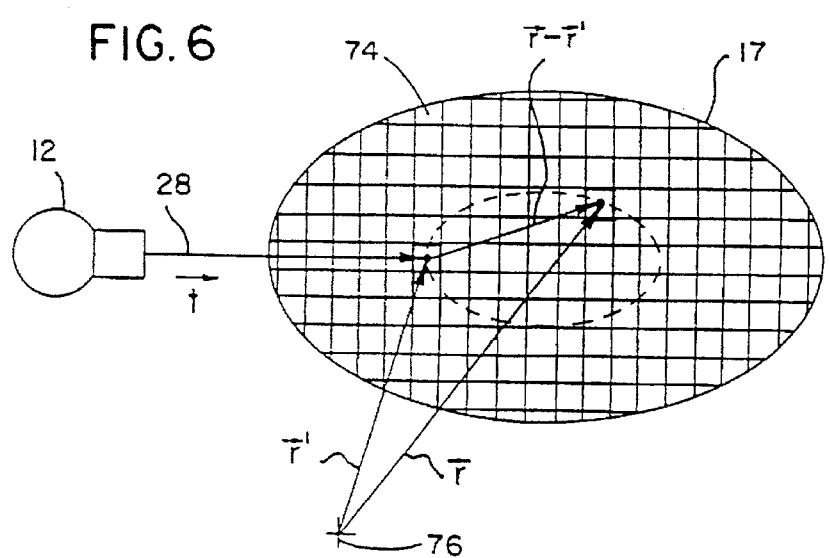
FIG. 6 is a diagrammatic representation of a patient receiving radiation therapy, showing the scatter kernel and the coordinate system used to describe the present invention.

Each element of the dose map 66 defines the dose desired at each of the plurality of volume elements 74 ("voxels") within a slice of the patient 17. Referring to FIG. 6, each voxel 74 of the patient 17 may be identified by a vector $\vec{r}$ defined from a given reference point 76. The dose at each voxel 74 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}'$; (where adjacent voxels $\vec{r}'$ include the voxel $\vec{r}$, i.e., the radiation received directly from the radiation source 12). The dose $D(\vec{r})$ for a given voxel $\vec{r}$ is given by the following formula:

$$D(\vec{r}) = \int T(\vec{r}') A(\vec{r} - \vec{r}') d^3 \vec{r}' \tag{1}$$

where $T(\vec{r}')$ is a value indicating the magnitude of the primary total energy released from $\vec{r}'$ per unit mass of that voxel $\vec{r}'$ and is called the "terma" (total energy released per unit mass).

For a monoenergetic external radiation source, the terma rate $\dot{T}(\vec{r})$ is described by:

$$\dot{T}(\vec{r}) = \frac{\mu}{\rho}(\vec{r}) E \phi(\vec{r}) dt \tag{2}$$

where μ/ρ is an effective mass attenuation value at the voxel $\vec{r}'$, E is the energy of the radiation photons in Joules, φ is the distribution of the fluence rate (flux density). The integration of energy times fluence rate over time is energy fluence $\Psi(\vec{r}')$ where:

$$\Psi(\vec{r}') = E \int \phi(\vec{r}') dt \tag{3}$$

hence $$T(\vec{r}) = \frac{\mu}{\rho}(\vec{r}) \Psi(\vec{r}) \tag{4}$$

Equation (4) basically relates how much energy from the ray 28 interacts with the voxel r'.

2. Convolution Kernel $A(\vec{r} - \vec{r}')$ is a convolution kernel describing non-stochastic energy transport or scattering in a uniform medium. $A(\vec{r} - \vec{r}')$ thus describes how the energy from each voxel $\vec{r}'$ spreads to contribute to the dose at voxel $\vec{r}$.

The kernel $A(\vec{r}-\vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}'$. The energy emitted from the terma of each voxel $\vec{r}'$ finds it source in a directed ray 28 from external radiation source 12 and thus $A(\vec{r}-\vec{r}')$ is generally anisotropic as suggested in FIG. 7, spreading outward away from the entry of ray 28. Energy conservation requires that:

$$\int A(\vec{r}')\, d^3\vec{r}' = 1.0 \tag{5}$$

That is, if the energy transferred by the primary interaction were all deposited on the interaction point, the kernel would be approximated as a delta function.

Figure 7:
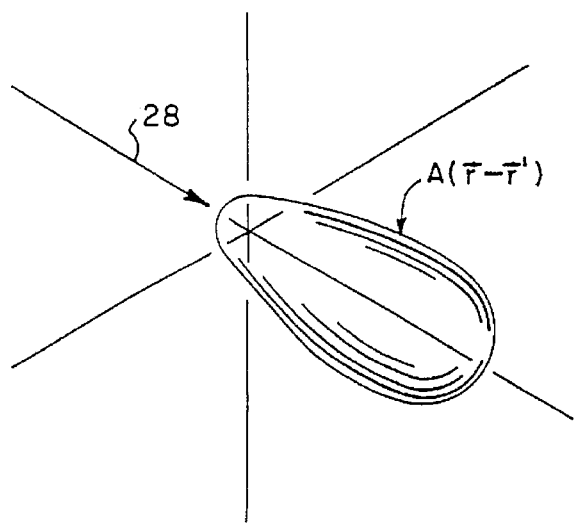
FIG. 7 is a perspective representation of a monodirectional scatter kernel associated with a radiation beam at one gantry angle.

Referring still to FIG. 7, the anisotropy of $A(\vec{r}-\vec{r}')$ is related to the gantry angle $\theta$ and thus of the angle of incidence of the ray 28 at $\vec{r}'$. If the gantry angles $\theta$ at which the patient 17 is irradiated are predetermined, a multidirection convolution kernel $B(\vec{r}-\vec{r}')$, shown in FIG. 8, may be created from weighted superimposition of the kernels $A(\vec{r}-\vec{r}')$.

Figure 8:
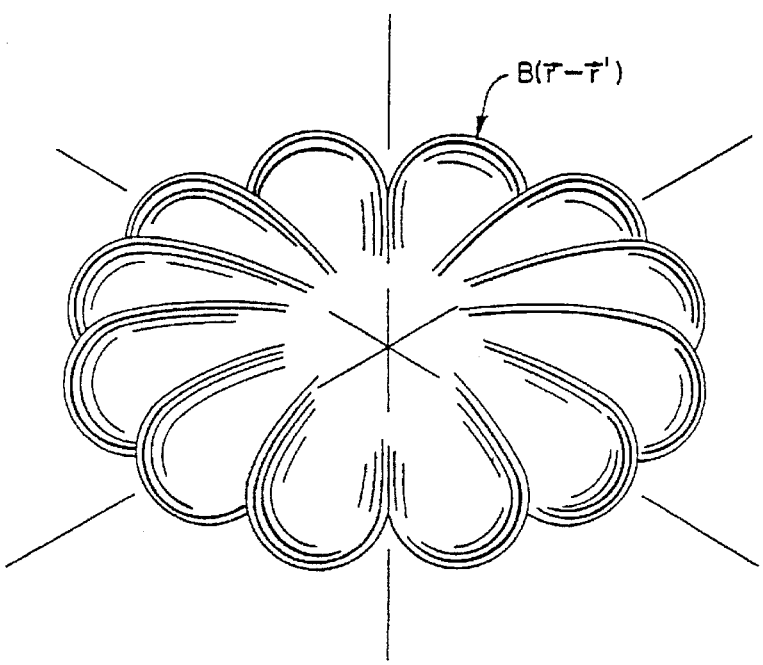
FIG. 8 is a perspective representation of a composite multidirectional scatter kernel associated with a plurality of radiation beams at multiple gantry angles.

Referring to FIG. 8, assuming that the spreading of radiation is approximately equal for all beam directions and the rays 28 from each gantry angle $\theta$ contribute equally to the terma at voxel $\vec{r}'$, then the multidirectional convolution kernel reduces to a "isotropic" form as follows:

$$B(\vec{r}-\vec{r}') = \frac{1}{n} \sum_{i=1}^{n} A(\vec{r}-\vec{r}')_i \tag{6}$$

where n is the number of discrete gantry angles from which rays 28 are projected.

For multiple rays 28 at different gantry angles, the total dose at a given voxel $\vec{r}$ is the sum of doses from each constituent beam is therefore:

$$D(\vec{r}) = \int T(\vec{r}') B(\vec{r}-\vec{r}')\, d^3 \vec{r}' \tag{7}$$

where $T(\vec{r}') = nT(\vec{r}')_i$, the latter term being the contributed portion of the terma for the ith gantry angle.

This simplification assumes that the contribution to the terma from each ray 28 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r}')\} \cdot F\{B(\vec{r}-\vec{r}')\}\} \tag{8}$$

where F and $F^{-1}$ symbolize Fourier and inverse Fourier transforms respectively. This simplification of equation (8) requires that the kernel $B(\vec{r}-\vec{r}')$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}')$ is correct only to a first order approximation. Typically, the kernel $B(\vec{r}-\vec{r}')$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 28 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of rays 28 that cross each voxel, caused by the geometry of a finite number of gantry angles and the fan orientation of the beam 14, affect spatial invariance. Problems arising from the fan orientation of the beam (in contrast to a parallel beam geometry) are largely solved if there is a full rotation of the gantry 44. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}')$ is assumed to be spatially invariant and the dose calculated according to equation (8).

Production of terma values from a desired dose map 66 is then simply the process of inverting equation (8) as follows:

$$T(\vec{r}) = F^{-1}\left\{ \frac{F\{D(\vec{r})\}}{F\{B(\vec{r}-\vec{r}')\}} \right\} \tag{9}$$

This inversion required that there be no significant "zeros" (typically at high frequencies) in the denominator term $F\{B(\vec{r}-\vec{r}')\}$ or more simply that the kernel $B(\vec{r}-\vec{r}')$ be spatially compact (i.e., the Fourier transform of a spatially compact kernel will have significant high frequency content). It has been determined by the present inventors that the kernels dictated for patients 17 are sufficiently compact to allow this Fourier deconvolution.

Figure 9:
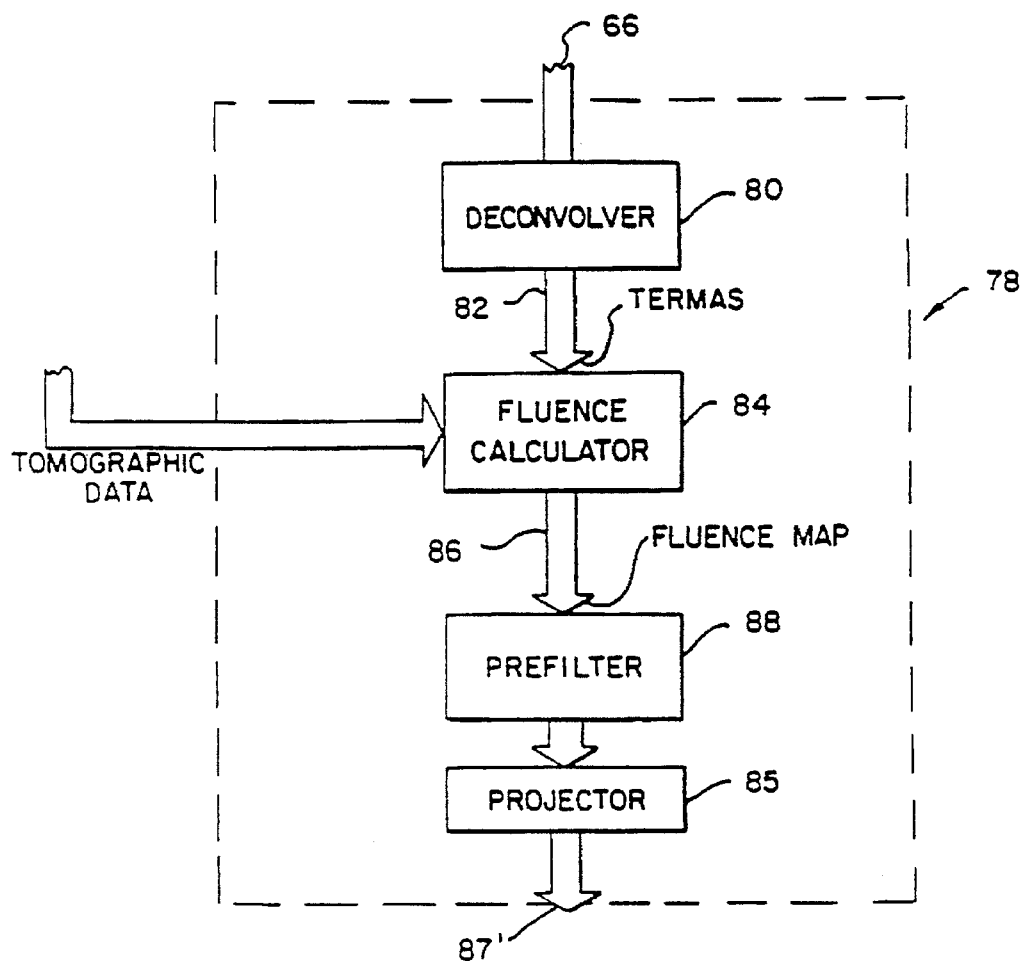
FIG. 9 is a block diagram depicting the fluence profile calculator which takes a desired dose map and calculates a fluence profile.
Figure 10:
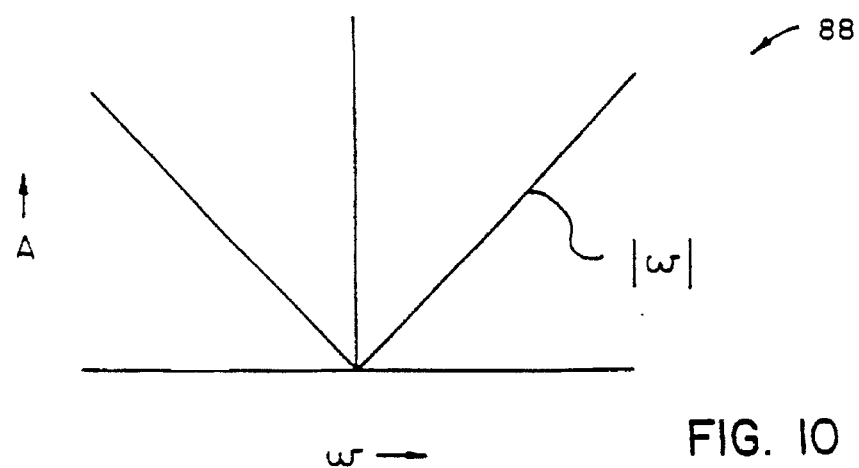
FIG. 10 is a graph showing the prefilter characteristics associated with the fluence profile calculator of FIG. 9.

Referring now to FIG. 9, this deconvolution to produce a terma map 82, giving the terma for each voxel $\vec{r}$, from the desired dose map 66, is represented by process block 80.

B. Converting Terma to Voxel Energy Fluence

Knowing the terma map 82, the energy fluence $\Psi(\vec{r}')$, which is a measure of the beam intensity, can be determined at each corresponding voxel by equation (4) from a knowledge of $\mu/\rho$ as follows:

$$\Psi(\vec{r}) = \frac{\frac{\mu}{\rho}(\vec{r})}{T(\vec{r})} \quad (10)$$

The value of μ/ρ may be estimated and considered a constant or actual μ/ρ may be deduced from the tomographic scan data collected by means of the tomographic imaging system 11, (shown in FIG. 4). In this manner and as illustrated by process block 84 of FIG. 9, a fluence may 86 giving the fluence at each point of the terma map may be determined.

C. Converting Voxel Energy Fluence to Energy Fluence Profile

The energy fluence $\Psi(\vec{r}')$ at each voxel $\vec{r}$ is related to the energy of the ray 28 exiting the compensator 22 by the relation:

$$\Psi(\vec{r}) = \Psi_0(\phi,\theta) e^{-\int \mu/\rho(\vec{r})\rho(\vec{r})\delta(p-\hat{r}\cdot\vec{r})dt} \left( \frac{SSD^2(\phi,\theta)}{|\vec{r}|^2} \right) \quad (11)$$

where $\Psi_o(\phi,\theta)$ is the energy fluence for a given ray 28 as described by $\delta(p-\hat{r}\cdot\vec{r})$ at the exit of the compensator 22 and serves to define the fluence profile of the compensator and θ and φ are the gantry angle and the offset angles of the ray 28 as previously described.

The exponential term represents the attenuation of the ray 28 from the exit of the compensator 22 to the voxel $\vec{r}$ caused by the mass of the patient 17 where by $\mu/\rho(\vec{r})$ is the attenuation for each voxel $\vec{r}$ along the ray 28, $\rho(\vec{r})$ is the density of each voxel $\vec{r}$, $SSD(\phi,\theta)$ is the distance between the exit of the compensator 22 and the surface of the patient 17, $\hat{r}$ is a unit vector along $\vec{r}$ (where the origin of $\vec{r}$ is now assumed to be the center of rotation of the gantry 45), and p is the perpendicular distance from the gantry's center of rotation 45 and the ray 28. The vector $\vec{t}$ is simply a vector along the ray 28 to provide an integration variable.

The fluence at each voxel $\vec{r}$ is related to the fluence of the radiation beam 14 emitted from the compensator 22 by equation (11). In the preferred embodiment, the density and attenuation of each voxel $\vec{r}$, $\mu/\rho(\vec{r}')$ and $\rho(\vec{r}')$ are assumed to be constant and the fan beam of radiation is approximated by a parallel beam, hence $$\frac{SSD^2(\phi,\theta)}{|\vec{r}|^2} = 1.$$

Borrowing from thematics of tomographic image reconstruction, the fluence map 86 may be "reverse" back projected (i.e. projected) by projector 85 to determine a fluence profile to be produced by the external-source necessary to generate the desired fluence map and hence dose.

This production is simply the opposite of a typical back projection used to form an image of a tomographic slice of a patient 17 from a series of projections taken in a tomographic imaging system. Because a projection is a line integral across a distribution, the energy fluence distribution for each voxel (equation (11)) is first differentiated with respect to the rayline $\vec{\tau}$:

$$\frac{d\Psi(\vec{r})}{dt} = \left[ \frac{\mu}{\rho}(\vec{r})\rho(\vec{r})\delta(p-\hat{r}\cdot\vec{r}) + \frac{2}{t} \right] \Psi(\vec{r}) \quad (12)$$

The line integral of $$\frac{d\Psi(\vec{r})}{dt}$$

along $\vec{\tau}$, corrected for attenuation and inverse-square fall off, then represents the projection operation and $\Psi_o(\phi,\theta)$, the fluence profile over the offset angles φ of each gantry angle θ, is:

$$\Psi_0(\phi,\theta) = \int \left[ \frac{\mu}{\rho} (\vec{r})\rho(\vec{r})\delta(p-\hat{r}\cdot\vec{r}) + \frac{2}{t} \right] \times \quad (13)$$

$$(\Psi(\vec{r})e^{+\int\mu/\rho(\vec{r})\rho(\vec{r})\delta(p-\hat{r}\cdot\vec{r})dt}) \left( \frac{|\vec{r}|^2}{SSD^2(\phi,\theta)0} \right) \times \delta(p-\hat{r}\cdot\vec{r})dt$$

The projection of equation (13) is represented by projector 85 in FIG. 9.

The projection process, for the purpose of computing fluence profiles for the compensator 22, differs in a fundamental way from the simple inverse of tomographic back projection. The difference is primarily in a concern for the sharpness in the transition of the dose between the irradiated tumorous tissue 68 and the healthy tissue 70. Sharpness in this transition region reduces the irradiation of healthy tissue 70 and is preferred over actual fidelity of the dose to the desired dose map 66.

For this reason, the fluence map 86 from the fluence calculator 84 is prefiltered as shown by process block 88 to produce a filtered fluence map $\Psi'(\phi,\theta)$ as follows:

$$\Psi'(\phi,\theta) = F-1\{F\{\Psi(\phi,\theta)|\omega|\}+ \quad (14)$$

where $\Psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile.

In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation:

$$\Psi(\phi,\theta) = \rho\{D(\vec{r})\} \otimes I(t) \quad (15)$$

where ρ refers to a projection operation and I(t) is the fast inversion filter. The $\otimes$ operators refers to a convolution operation such as would normally be done in Fourier space using a fast Fourier transformation.

Referring still to FIG. 9, the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 66. The fluence profile calculator 78 may use the Fourier convolution of equation (9) in the estimate of the fluence profiles at this stage, accepting minor inaccuracies in that process, to be corrected at a later stage, as will be described below.

D. Iteration

Figure 11:
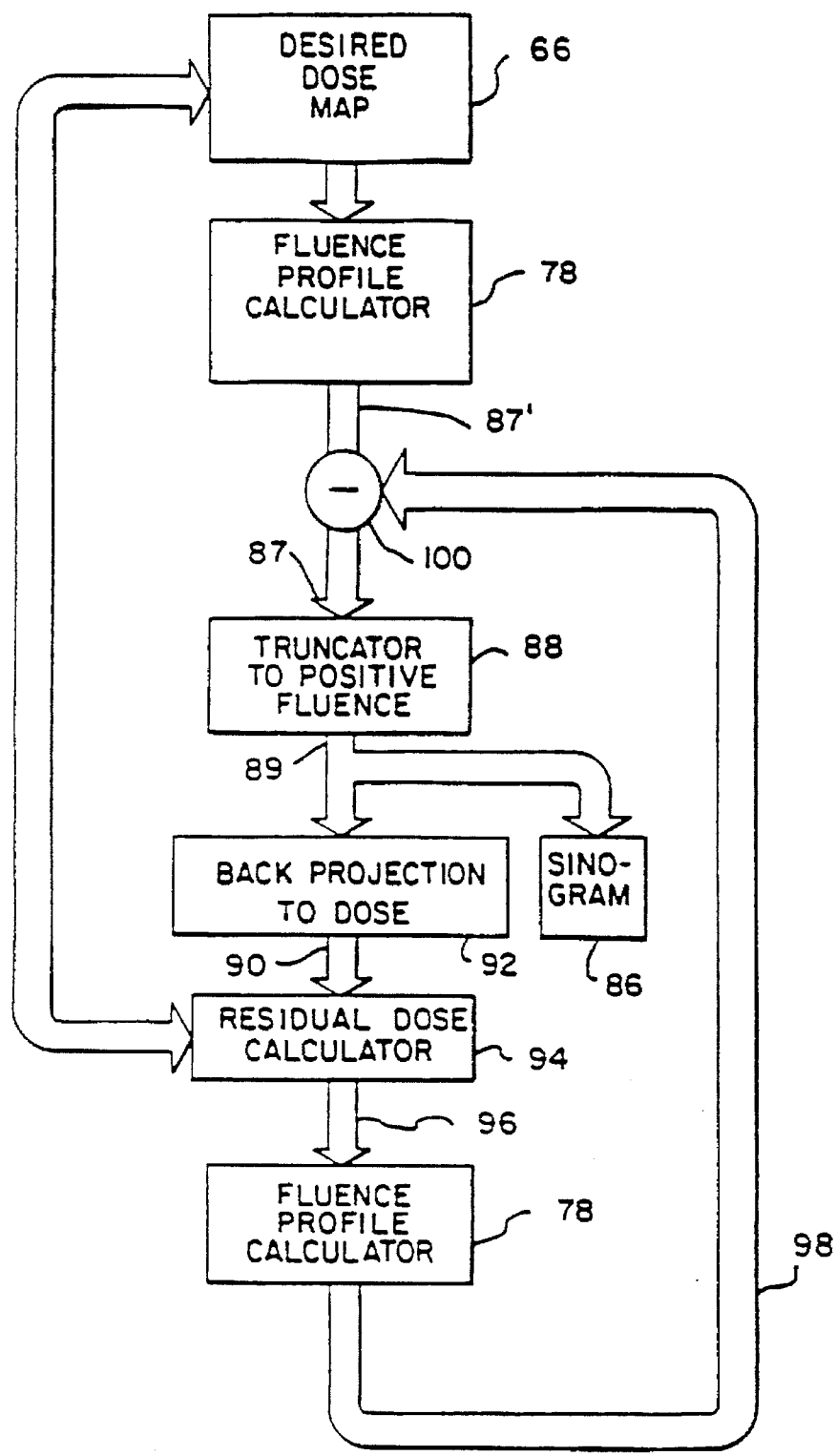
FIG. 11 is a block diagram depicting the overall iterative method of controlling the compensator of the present invention, employing the fluence profile calculation method of FIG. 9.

Referring now to FIG. 11, the fluence profile calculator 78 converts the desired dose map 66 to an estimated treatment sinogram 87', however the fluence profiles of this estimated treatment sinogram 87' may not be used to control the compensator 22 because, in general, the estimated treatment sinogram 87 will include positive and negative values of fluence. Only positive values of fluence are physically realizable by the compensator 22; a negative value of fluence would represent a ray 28 that absorbed radiation along its path which is physically unrealizable.

Accordingly, at process block 88, the fluence values of the estimated treatment sinogram 87' no longer produces the desired dose map.

The amount of error resulting from the truncation producing the positive fluence profiles 89 is determined by back projecting the positive fluence values 89 to an actual dose map 90 deviating from the desired dose map 66. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 11.

In this back projection, the assumption of spatial invariance of the convolution kernel $B(\vec{r} - \vec{r}')$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 66 to produce residual dose map 96 as indicated by process block 94. In the preferred embodiment, the comparison subtracts from the values of each voxel $\vec{r}$ of the actual dose map 90, the greater of: a) the corresponding value of desired dose map 66, or b) a predetermined upper dose constraint. The predetermined upper dose constraint is a threshold number that is deemed an acceptable dose to tumorous tissue 68. Clearly, other methods of quantifying the difference between the desired dose map and the actual dose map will be apparent from this description to those of ordinary skill in the art.

Figure 12A:
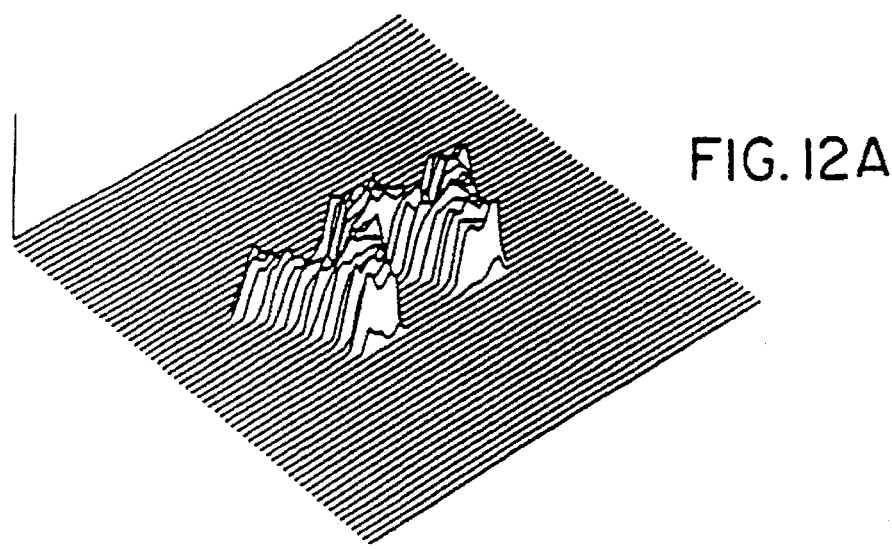
FIGS. 12(a)–(c) are perspective views of plots showing the error between the desired dose distribution and the actual dose distribution obtained with the present invention for one, two and four steps of iteration respectively.
Figure 12B:
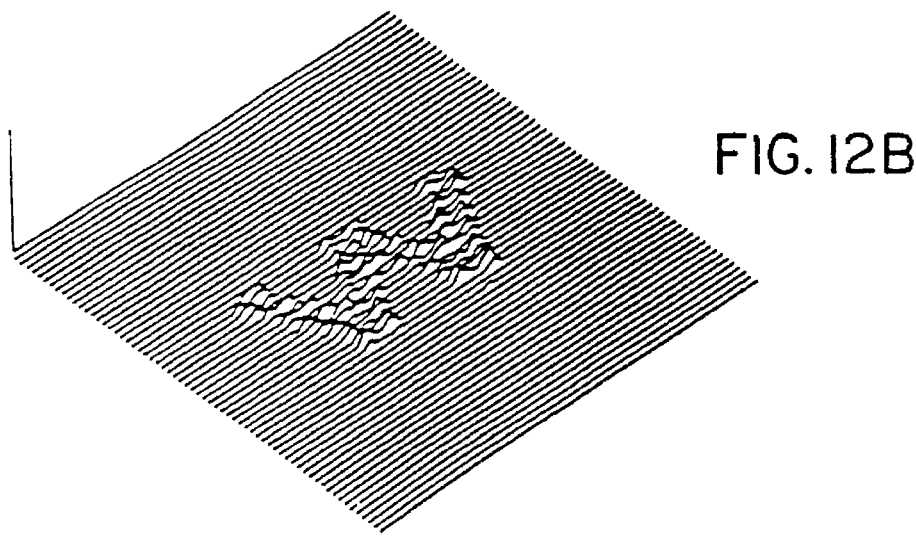
Figure 12C:
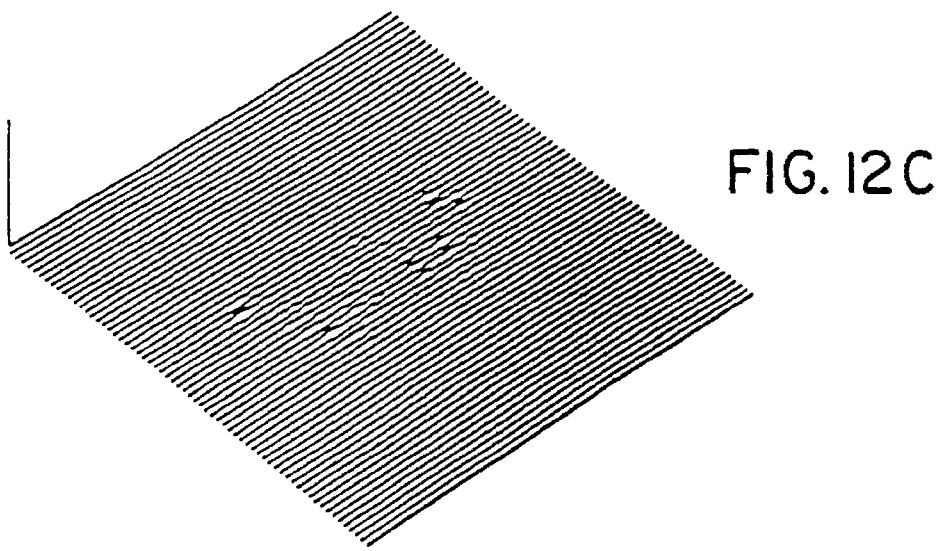

The result of this comparison process 94 is to produce a residual dose map 96 shown in FIG. 12(a). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 87.

As shown in FIG. 11, this new estimated treatment sinogram 87 is repeatedly operated on by process block 88, 92, 94 and 78 for a predetermined number of iterations, the magnitude of the error fluence profile 98 values decreasing suitable low error fluence profile 98 values decreasing suitably low error fluence profile 98 is obtained.

The new estimated fluence profile 87 is then truncated per process block 88 to produce a final sinogram 91 for use in controlling the compensator 22 as previously described.

Figure 5B:
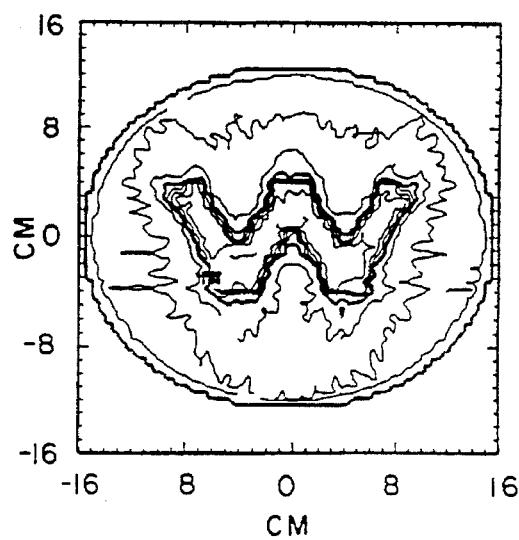
Figure 5C:
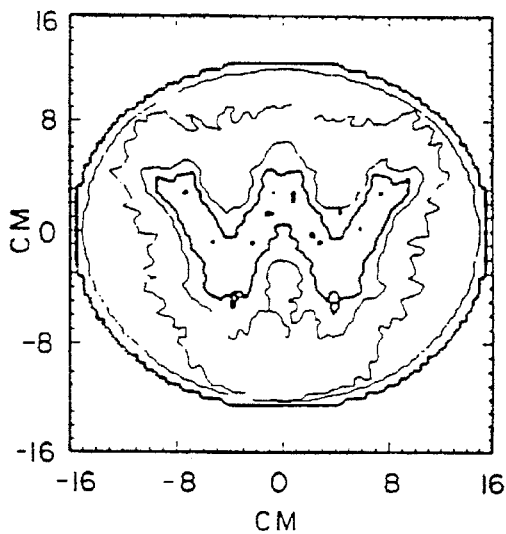
Figure 5D:
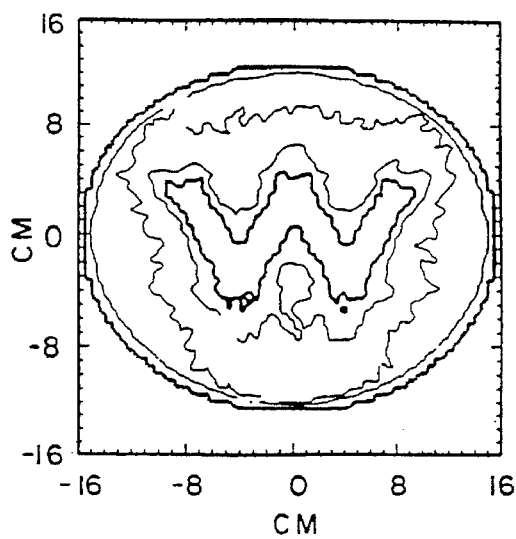

Referring again to FIGS. 5(b), (c) and (d), dose maps obtained by the present invention corresponding to a desired dose map 66 of FIG. 5(a) are shown after: one iteration (FIG. 5(B)); two iterations (FIG. 5(c)); and ten iterations (FIG. 5(d)). The variations in dose in the target volume shown in FIG. 5(d) are plus or minus 2% about the predetermined upper limit of 1,000 cGy.

IV. Human Interface

Figure 15:
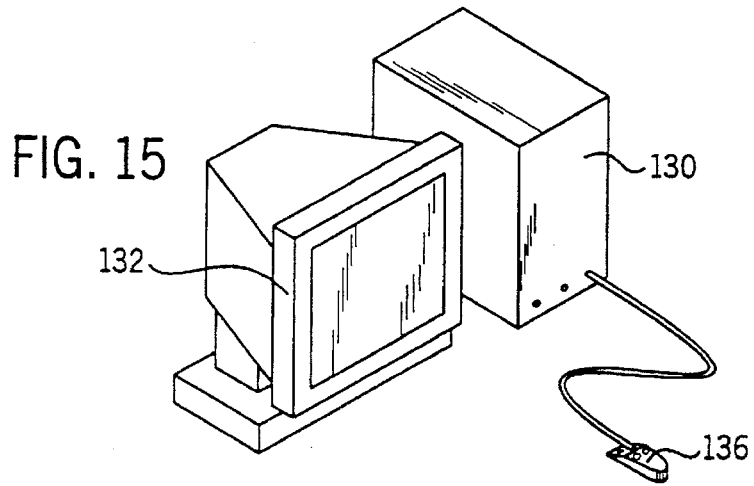
FIG. 15 is a schematic representation of a human interface according to the present invention.

Referring now to FIGS. 14 and 15, after a CT machine has been used to generate the tomographic images 117–120 corresponding to different patient slices to be treated, an operator must identify regions to be irradiated and others that preferably receive little or no radiation. To this end, the present invention includes a computer 130 having a display screen 132 which may be either a colored or a gray-scale device, a mouse 136 or other manual cursor control device as well known in the computer arts, sufficient random access memory (RAM) to store massive quantities of data, and a high powered processor capable of quickly processing the equations above.

Figure 17:
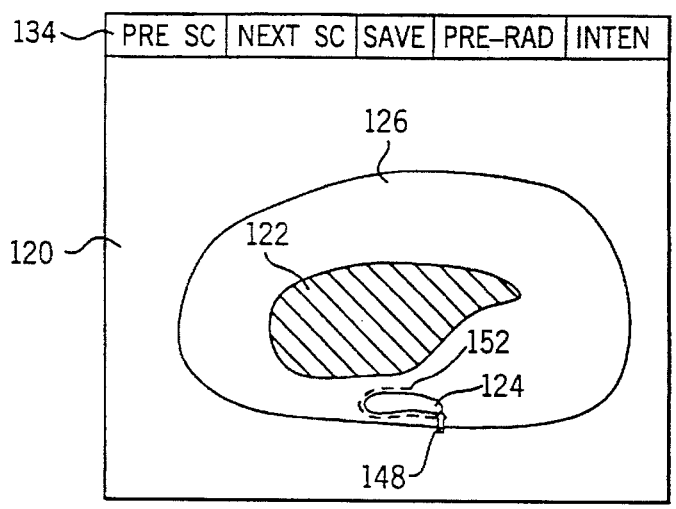
FIG. 17 is a plan view similar to that of FIG. 16 with one irradiation region identified.

Referring to FIGS. 14 and 15, after tomographic images 117–120 have been generated and data defining each image has been stored in the computer RAM, the mouse 136 is used to access the RAM and display one tomographic image 117, 118, 119, or 120 at a time on display screen 132. To this end, the display screen 132 includes a menu bar 134 stretching across the top of the screen 132 as seen in FIG. 17. The operator may move the cursor arrow 148 into a position identifying one of the menu options. By clicking one of the mouse buttons (i.e. with the left or right) with the cursor arrow 148 inside an option box, the operator can select various interface functions. Initial menu functions which appear on the display screen 132 when the interface is turned on are "PPE SC" for previous screen, "NEXT SC" for next screen, "SAVE", "PRE-RAD" for pre-radiation test, and "INTEN" for intensity adjustment. Each of these functions and certain others which appear on later screens will be described in detail below.

Figure 16:
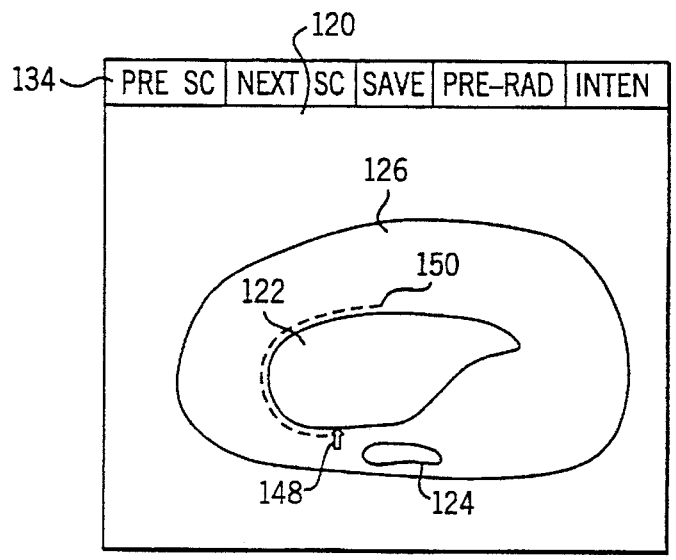
FIG. 16 is a plan view of one of the hypothetical tomographic images shown in FIG. 14 including a cursor arrow according to the present invention.

Referring to FIG. 16, with the interface turned on, to display a tomographic image on the screen 132, the operator moves the cursor arrow 148 to the NEXT SC function and clicks the left mouse button twice to select the next screen function. This will bring up the tomographic image corresponding to an end slice of the treatment region 106 (see FIG. 13). To scroll through patient slice images, the operator simply continues to select the NEXT SC function. To move back through slice images, the operator can select the PREV SC function. Typically, only ten to thirty distinct patient slices will be specified, the number depending upon the size of the tumorous region to be treated and the degree of precision required under the specific circumstances of a therapy session (i.e. proximity of the tumorous region with respect to sensitive organs or tissue).

Referring to FIG. 16 with tomographic image 120 displayed, three distinct regions can be identified including a tumorous region 122, a spinal region 124, and the non-tumorous tissue region 126. For purposes of explaining the inventive human interface, in a hypothetical therapy planning session it will be assumed that during an irradiation session, ten units of radiation should be directed at each point located within the tumorous region 122 and that minimal radiation should be directed at the non-tumorous regions. In addition, ideally, zero units of radiation would be directed toward the spinal region, however, it would be acceptable if less than 0.5 units of total radiation were directed at the spinal region 124.

Referring still to FIGS. 15 and 16, with tomographic image 120 displayed, an operator uses the mouse 136 to direct the cursor arrow 148 to a boundary between two different regions (i.e., in this case, between the tumor and non-tumor regions or between the non-tumor regions and the spinal region). With the cursor arrow 148 on a boundary, the operator clicks on the left mouse button twice indicating that the operator intends to trace a region of interest. In FIG. 16, a trace is identified by the dotted line which begins at initial point 150. After clicking twice, the operator moves the cursor arrow 148 about the boundary of the region to be traced until the entire boundary has been circumscribed and the cursor arrow 148 is back at the initial point 150. In FIG. 16, the first region traced is the tumorous region 122. When the initial point 150 is reached, the operator clicks twice on the other mouse button (e.g., the right mouse button) indicating that the trace is completed and the tumorous region 122 has been defined. Referring also to FIG. 17, after indicating that trace has been completed, the computer will fill in the area identified by the trace using standard area filling computer programs as well known in the art.

Figure 19:
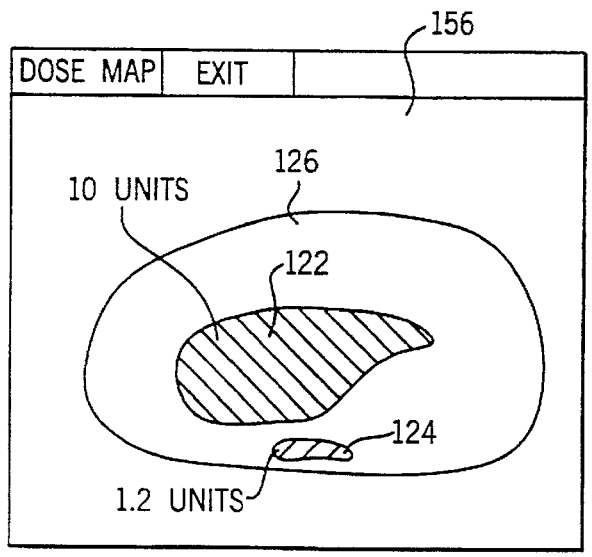
FIG. 19 is a plan view of a test pre-irradiation tomographic image.

Next, the operator uses the mouse to move the cursor arrow 148 to a boundary defining another region of interest, in this case the spinal region 124. After clicking on the left mouse button twice at initial point 152 to indicate that a trace is to begin, the operator maneuvers the cursor arrow 148 around the boundary defining the spinal region 124 until the entire region has been circumscribed and the cursor arrow 148 points at the initial point 152. At this time, the operator clicks twice on the right mouse button indicating that the trace has been completed and the spinal region 124 has been defined. Referring also to FIG. 19, when the right mouse button is pressed, as before, the computer fills the region circumscribed so that the operator can identify the region easily.

At this point, because the operator has defined two regions of interest, the computer can identify the third region (i.e., the non-tumorous area 126). Where additional regions of interest (i.e. other organ or tumorous parts) exist, the operator would trace each region using the cursor arrow as described above.

Figure 18:
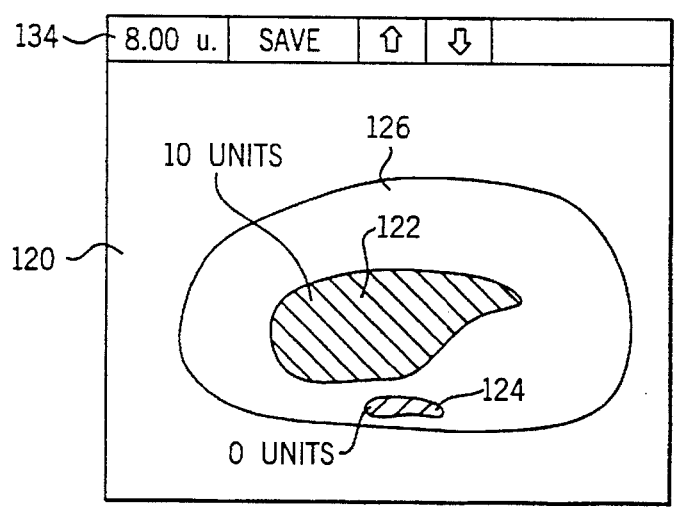
FIG. 18 is a plan view-similar to that of FIG. 16 with two irradiation zones identified.

After all the regions of interest have been defined, the operator can use the mouse to select desired radiation doses for each of the defined regions of interest. To this end, referring again to FIG. 16, the operator uses the mouse to move the cursor arrow 148 into the INTEN (i.e. intensity select) box of menu 134 and clicks twice on the left mouse button. The computer Will then display a standard radiation intensity value in the upper left hand corner of the display screen as seen in FIG. 18. For example, where the range of possible radiation dose during a single irradiation session is between zero and sixteen radiation units, the standard value might be 8.00 units. In addition to the intensity box, the menu would also include an up arrow for increasing intensity, a down arrow for decreasing intensity, and a SAVE function for saving a defined dose map. Next the operator uses the mouse to place the cursor arrow 148 within one of the regions of interest. With the arrow 148 in a region, the operator clicks twice on the left mouse button indicating that the operator wishes to identify the quantum of radiation to be ideally delivered to the region during a subsequent therapy session. With the tumorous region 122 identified, the operator would use the mouse to direct the cursor arrow 148 to either the up or the down function arrows on menu 134. In the present case, because 10 units of radiation is desired in the tumors region 122, the operator would select the up function from the menu 134 until the intensity value increased from 8 units to ten units.

Next, the operator would use the mouse to move the cursor arrow 148 into the spinal region 124 and would again click twice on the left mouse button indicating that the operator intends to define the radiation to be delivered to the spinal area 124. With the spinal area 124 selected, again the average radiation value of 8 units would appear in the left upper corner which could be adjusted as described above using the up and down arrow functions selected via the mouse. As desired, the operator would decrease the intensity value in the upper left hand corner until it reads zero units.

This process would be steps through again for the non-tumorous tissue identifying specific dose limitation. At this point, a desired dose map for irradiating the patient slice associated with tomographic image 120 has been defined. To save a dose map, the operator selects the SAVE option from menu 134. As described above, the therapy planning software can now be used to develop a treatment sinogram associated with tomographic image 120.

Unfortunately, even after a plurality of iterations to correct for scattered radiation effects, there may be some deviation from the desired dose maps in the amount of radiation absorbed by various regions within a patient slice associated with a specific tomographic image. Referring to FIG. 19, in the present case, this may mean that unintended radiation might subtend and be absorbed by the spinal region 124. After sinogram iterations to correct for dose errors, the computer can be used to effectively smear fluence profiles across a plane generating a pre-radiation test tomographic image indicating the expected dispersion of radiation given a specific sinogram. In the hypothetical pre-radiation test tomographic image shown in FIG. 19, despite error reducing fluence profile iterations, an error in spinal region 124 dose of 1.2 radiation units still exist. Assuming that 1.2 units is not acceptable, in the spinal region 124, the operator can then use the interface to alter the units of radiation to be delivered to various regions in an effort to lower the amount of radiation delivered to the spinal region.

Referring still to FIG. 19, when a pre-radiation test tomographic image is displayed, the menu 134 includes two functions, a DOSE MAP function, and an EXIT function. To alter a dose map to eliminate unacceptable radiation identified on a pre-radiation image, the operator selects the DOSE MAP function which returns the operator to the image shown in FIG. 18. The operator can then use the mouse to select any region of interest for changing desired dose. For example, the operator may choose the tumorous region 122, clicking on that region twice. At this point the intensity box in the menu 134 would read 10 units, the value earlier specified. This value would be altered as described above using the up and down arrow functions.

In the present case, because the only region identified as affirmatively receiving radiation is the tumorous region 122, to lower the radiation within the spinal region 124 the degree of radiation within the tumorous region 122 must be lower. By selecting 8 instead of 10 units for the tumorous region 122, the spinal region 124 radiation should be lowered. In the hypothetical being discussed here, it will be assumed that by lowering the radiation delivered to the tumorous region 122 the radiation delivered to the spinal region 124 is lowered to 0.5 units, a value which, although not ideal, would be acceptable under the circumstances. The operator saves the new dose map by selecting the SAVE function from menu 134.

To insure that none of the regions of interest in the patient slice will be over-radiated, given the new dose map, the operator again uses the mouse to select the pre-radiation function from menu 134 indicating to the computer that a second pre-radiation test tomographic image should be generated pursuant to the new dose map. In this case, upon a perusal of the pre-radiation test tomographic image (not shown), the image indicating that the tumorous area 122 will receive 8 units of radiation while the spinal area 124 will receive 0.5 units, the operator accepts the dose map and selects the EXIT function via the mouse which returns the operator to the tomographic image screen as in FIG. 17 with the initial menu bar 134.

Referring also to FIG. 14, next, the operator uses the mouse to select the NEXT SC function to bring up the next tomographic image 119 and follows the same dose map identifying protocol described above for image 119 until an acceptable pre-radiation test tomographic image has been derived for image 119. This process is repeated for each of the tomographic images corresponding to the tumor, each resulting dose map and sinogram being saved in the computer memory.

After acceptable treatment sinograms have been generated and saved for each of the tomographic images, the patient 100 is placed on the treatment table 101 in a supine orientation. The patient is moved along an axis parallel to the length of the table 101 until fiducial points on the patient are precisely located relative to the gantry so that the radiation beam subtends a single known slice of the patient. The sinogram corresponding to the patient slice subtended by the fan beam is accessed by the computer for controlling the compensator as described above. Next, the radiation source is rotate around the gantry and the intensity of each ray of the fan beam is altered according to the fluence profiles which make up the treatment sinogram.

Referring also to FIG. 4, the radiation array detector 50' which is at all times opposite the radiation source 12, can be programmed to receive radiation from each of the rays within the fan beam at each gantry angle as radiation exits the patient 17. As described in U.S. Pat. No. 5,394,452, which issued on Feb. 28, 1995, the specification of which is incorporated herein by reference, the radiation values detected by the detector array 50' may be compared to the known values of radiation within each ray of the fan beam to determine the quantum of radiation absorbed within the patient along each ray of the fan beam from each gantry angle. The computer can use this data to generate a post-radiation tomographic image corresponding to each patient slice after a therapy session indicating the intensity of absorbed radiation within all regions of interest.

Figure 20:
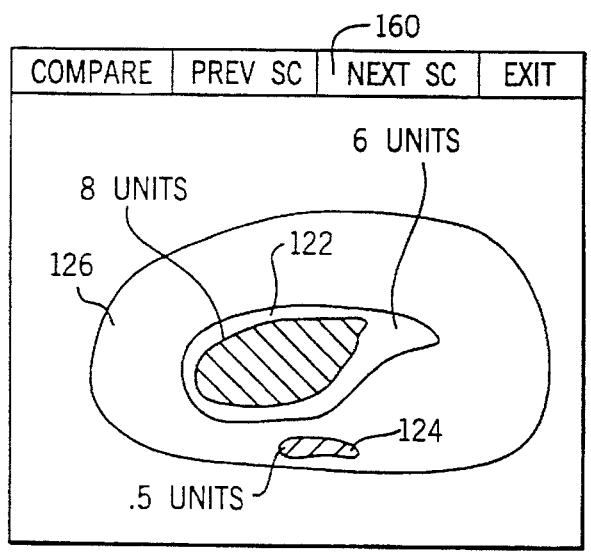
FIG. 20 is a plan view of a post-irradiation tomographic image.

Referring to FIG. 20, after a therapy session, the operator can display each post-radiation tomographic image 160 on the display screen 132 separately to identify any radiation errors (i.e. deviation from the desired dose map). Unfortunately, despite sinogram iterations and dose map alterations to produce desired dose maps, it is often the case that an actual dose map may vary somewhat from a desired dose map. For example, referring to FIG. 21, often the circumferential area of a tumor or a distal peninsular area may receive less radiation than other portions. In hypothetical FIG. 20, 8 units have been delivered to the central portion of the tumorous area 122 whereas only 6 units have been delivered to the distal peninsular and outer portions of the tumorous area 122. In this situation, an operator can use the interface to display the post-radiation tomographic image 160 where radiation errors which occurred during a prior therapy session can be observed.

When a post-radiation image 160 is provided on screen 132, the menu 134 includes EXIT, COMPARE, NEXT SC, and PRE SC functions. By selecting the COMPARE function via the mouse, the computer will compare the post-radiation tomographic image 160 with the pre-radiation desired dose map (see FIG. 18) and produce a post-radiation dose error image 166 as in FIG. 21. In this case, because the distal peninsular and circumferential portions of the tumorous area 122 were under-radiated during the previous radiation therapy session, the dose error image 166 identifies a ring 168 around the circumferential portion of the tumorous area 122. This post-radiation dose error image 166 is to be used in subsequent therapy sessions to adjust delivered radiation accordingly.

To this end, when the post-radiation dose error image 166 is displayed, the menu 134 includes a DOSE COMP function which automatically generates a new dose map for a patient slice which compensates for dose delivery errors during the previous radiation session.

Figure 21:
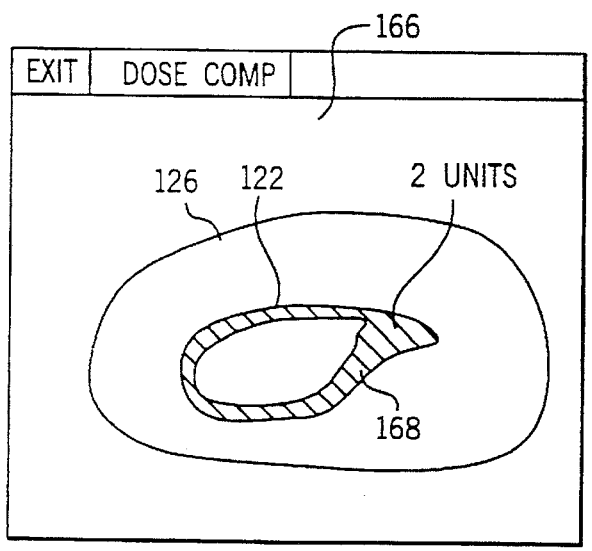
FIG. 21 is a plan view of a post-irradiation error tomographic image.
Figure 22:
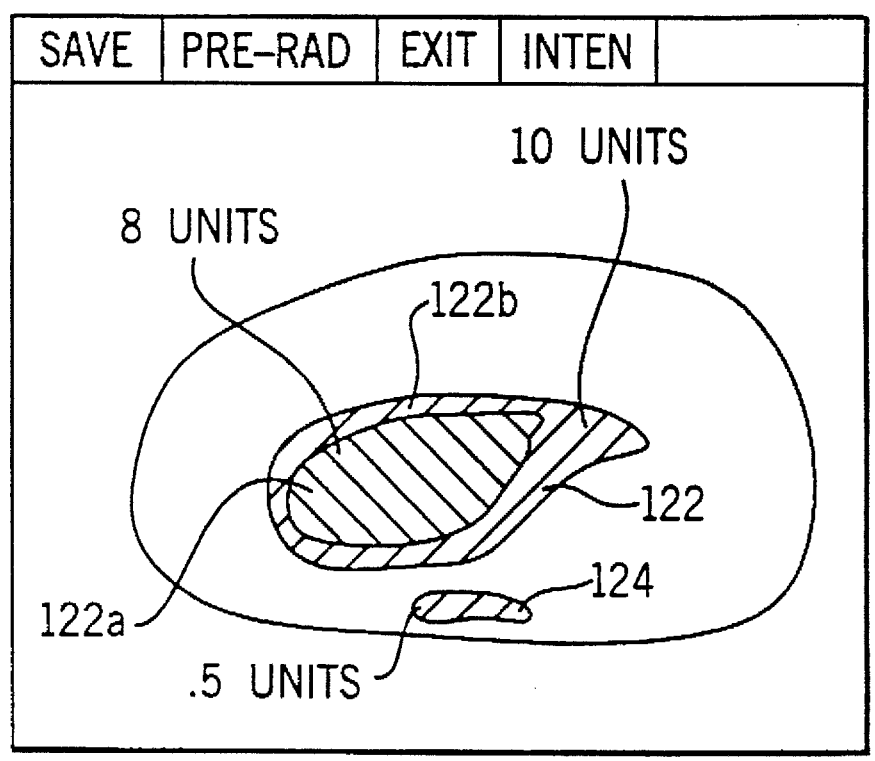
FIG. 22 is a plan view of an error compensating dose map.

Referring to FIG. 22, assuming that the average radiation to be delivered to a tumorous region and a spinal region over the course of two therapy sessions is 8 units and 0.5 units respectively, and given the hypothetical dose error image 166 of FIG. 21, an adjusted second dose map to be used during a second therapy session would include 0.5 units for the spinal region 124, 8 units for a central portion 122a of the tumorous area 122, and 10 units (i.e., the desired 8 units plus the erroneous 2 units from the tomographic error image of FIG. 21) for the external portions 122b of the tumorous region 122.

By selecting the DOSE COMP function, the computer automatically mathematically combines the desired dose map and the actual dose map to provide the compensating new dose map to be used during the next therapy session. Again after this second dose map has been generated, the operator can use the interface to run a pre-radiation test therapy session generating a pre-radiation test tomographic image identifying likely dose dispersion the subsequent second therapy session. If the dose dispersion is acceptable, the second dose map can be saved in RAM and the operator can move on to observe other post-radiation tomographic images from the first therapy session to identify alterations required in the second therapy session. As above, the NEXT SC and PRE SC functions can be selected using the mouse to scroll back and forth between post-radiation tomographic images. When desired, the operator can select the EXIT function from the menu indicating to the computer that the operator wishes to exit the post-radiation image viewing mode.

The above description has been that of a preferred embodiment of the present invention. It will occur to those who practice the art that many modifications may be made without departing from the spirit and scope of the invention. For example, the method for planning radiation therapy is not limited to a particular radiation source but may be used with any radiation source which may be decomposed into separately attenuated radiation rays. While the tracing means has been described as a conventional mouse, any type of tracing means could be used. In addition, while no key board has been described above, clearly, instead of using a display menu and mouse to select options, a key board could be used, the novelty of the present invention being in the method of displaying and tracing images as opposed to specific function selection devices. Furthermore, the inventive apparatus and method of generating radiation dose maps could be used to identify other radiation limitations. For example, the interface could be used to specify maximum limitations within a region of interest (i.e. no more than 0.5 units of radiation) or minimum limits (i.e. no less than 8 units of radiation) or precise units which must be met (i.e. exactly 8 units of radiation). With these types of limitation, the computer could then automatically adjust other regions to generate an optimal dose map meeting the required constraints and could produce pre-radiation test sinograms for operator observation. In order to apprise the public of the various embodiments that may fall within the scope of the invention, the following claims are made:

We claim:

1. A method for radiation treatment planning comprising the steps of:

(a) obtaining an x-ray computed tomography image of a slice in a slice plane through a body including a portion of a tumor to be treated;

(b) displaying the x-ray computed tomography image of the slice on a display screen of a computer;

(c) tracing at least one zone on the displayed image of the slice by means of a manual cursor control device communicating with the computer;

(d) entering into the computer a desired dose limit for the at least one zone to produce a dose map; and (e) determining a treatment sinogram of fluence profiles for radiation to be projected along the slice plane at a range of angles about the patient within the slice plane based on the dose map so defined.

2. The method as recited in claim 1 wherein the step of obtaining an x-ray computer tomography image includes the step of obtaining a plurality of x-ray images in parallel slice planes through the body, each slice including a portion of the tumor to be treated, and, wherein the method further includes the step of repeating each of steps (b) through (e) for each of the x-ray images.

3. The method of claim 1 wherein step (c) traces at least three zones and where step (d) enters different desired dose limits for the three zones.

4. The method as recited in claim 1 wherein the step of entering a desired dose limit into the computer includes the steps of entering a dose limit into the computer corresponding to each of the zones identified during the tracing step.

5. The method as recited in claim 4 wherein the step of entering the dose limits includes entering a limit of zero dose for at least one zone.

6. An apparatus for radiation treatment planning to be used with a computed tomography machine capable of producing at least one x-ray computer tomography image of a slice in a slice plane through the body of a patient, the slice including a portion of a tumor to be treated, the apparatus comprising:

a display for displaying the x-ray computed tomography image of the slice;

a tracer;

a dose identifier; and a computing means connected to the display, the tracer, and the dose identifier, the computing means allowing the tracer to be used to trace at least one irradiation zone on the image displayed on the display, allowing the dose identifier to be used to specify at least one irradiation dose for at least one irradiation zone to produce a desired dose map, and, based on the desired dose map, the computing means generating a treatment sinogram of fluence profiles for radiation to be projected along the slice plane at a range of angles about the patient within the slice plane.

7. The apparatus as recited in claim 6 wherein the dose identifier is used to identify a dose in each irradiation zone identified.

8. The apparatus as recited in claim 6 wherein the dose identifier is used to identify at least one irradiation zone wherein the dose is zero.

9. The apparatus as recited in claim 6 wherein the tracer is a computer mouse.

10. The apparatus as recited in claim 6 wherein the computed tomography machine provides a plurality of x-ray computed tomography images in parallel slice planes through the patients body, each slice including a portion of the tumor to be treated, and, wherein the display, tracer, dose identifier and computing means are used together to plan radiation treatment for each of the parallel slices.

11. The apparatus of claim 6 wherein the computing means allows the tracer to be used to trace at least three irradiation zones and the dose identifier to specify at least three different irradiation doses for the zones.

12. The apparatus as recited in claim 6 also used with a radiation detector which can determine the magnitude of radiation absorbed within a patient along each ray of a fan beam, wherein the tomographic machine is also used to produce a post-radiation dose map corresponding to the radiation magnitude data provided by the detector, the display being used for displaying the post-radiation dose map for viewing by an operator.

13. The apparatus as recited in claim 12 wherein the computer can correlate corresponding desired and post-radiation dose maps to generate a post-radiation dose error image, the display being useable for displaying the post-radiation dose error image.

14. The apparatus as recited in claim 13 wherein the computer can correlate a corresponding post-radiation dose error image and a desired dose map to provide a new dose map for use in a subsequent irradiation session, the new dose map compensating for the post-radiation dose error image.

* * * * *

UNITED STATES PATENT AND TRADEMARK OFFICE
CERTIFICATE OF CORRECTION

PATENT NO. : 5,661,773
DATED : August 26, 1997
INVENTOR(S) : Swerdloff et al.

It is certified that error appears in the above-identified patent and that said Letters Patent is hereby corrected as shown below:

Col. 9, line 58,
$F^{-1}\{f\{F(\vec{r}')\}\cdot F\{B(\vec{r}-\vec{r}')\}\}$

*Should be*
$F^{-1}\{F\{T(\vec{r}')\}\cdot F\{B(\vec{r}-\vec{r}')\}\}$

Col. 11, Line 16, $\vec{r}$       Should be $\vec{r}'$

Col. 12, line 10, $\vec{t}$       Should be $\vec{t}$

Signed and Sealed this

Seventeenth Day of February, 1998

*Attest:*

BRUCE LEHMAN

*Attesting Officer*       *Commissioner of Patents and Trademarks*